(12) United States Patent
Kessels et al.

(10) Patent No.: US 10,842,718 B2
(45) Date of Patent: Nov. 24, 2020

(54) FEEDING SYSTEM FOR AN INFANT AND METHOD OF USING SUCH A SYSTEM

(71) Applicant: KONINKLIJKE PHILIPS N.V., Eindhoven (NL)

(72) Inventors: Marijn Kessels, Eindhoven (NL); Pia Petronella Maria Donkers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 303 days.

(21) Appl. No.: 15/754,310

(22) PCT Filed: Aug. 29, 2016

(86) PCT No.: PCT/EP2016/070298
§ 371 (c)(1),
(2) Date: Feb. 22, 2018

(87) PCT Pub. No.: WO2017/045902
PCT Pub. Date: Mar. 23, 2017

(65) Prior Publication Data
US 2018/0243173 A1 Aug. 30, 2018

(30) Foreign Application Priority Data
Sep. 14, 2015 (EP) .................................... 15184981

(51) Int. Cl.
*A61J 9/02* (2006.01)
*G01F 15/06* (2006.01)
(Continued)

(52) U.S. Cl.
CPC . *A61J 9/02* (2013.01); *A61J 9/00* (2013.01); *G01F 15/063* (2013.01); *G16H 20/60* (2018.01); *A61J 9/06* (2013.01); *A61J 11/00* (2013.01); *A61J 2200/70* (2013.01); *A61J 2200/72* (2013.01); *G01F 15/001* (2013.01); *G01F 15/003* (2013.01); *G01F 15/066* (2013.01)

(58) Field of Classification Search
CPC .. A61J 9/02; A61J 9/00; A61J 2200/70; A61J 9/06; A61J 2200/72; A61J 11/00; A61J 2200/74; G16H 20/60; G01F 15/063; G01F 15/003; G01F 15/066; G01F 15/001
See application file for complete search history.

(56) References Cited

U.S. PATENT DOCUMENTS 6,991,122 B2  1/2006  Holley
8,959,697 B2  2/2015  Yu
(Continued)

FOREIGN PATENT DOCUMENTS

CN   102988184        3/2013
EP   1718197 B1      11/2006
(Continued)

*Primary Examiner* — Mohammad K Islam

(57) ABSTRACT

The present invention relates to a feeding system (1) for infants comprising a bottle (2) for storing and releasing a fluid, at least one sensor (10, 20, 30) arranged in or at the bottle (2) for measuring one or more bottle parameters, a data processing unit (12, 22, 32) for processing the measured bottle parameters to generate an advice related to at least one bottle parameter, and an indicator (13, 23, 33) for issuing said advice to a user of the feeding system (1).

20 Claims, 4 Drawing Sheets

(51) Int. Cl.
*G16H 20/60* (2018.01)
*A61J 9/00* (2006.01)
*A61J 11/00* (2006.01)
*A61J 9/06* (2006.01)
*G01F 15/00* (2006.01)

(56) References Cited

U.S. PATENT DOCUMENTS

| | | | |
|---|---|---|---|
| 9,561,002 B2* | 2/2017 | Lau | A61B 5/14542 |
| 2006/0042550 A1* | 3/2006 | Hoshiba | A01K 9/005 |
| | | | 119/71 |
| 2006/0129127 A1* | 6/2006 | Ruth | A61J 9/00 |
| | | | 604/514 |
| 2006/0261233 A1* | 11/2006 | Williams | A61J 9/00 |
| | | | 248/311.2 |
| 2008/0039778 A1 | 2/2008 | Goldie | |
| 2010/0308003 A1* | 12/2010 | Morrill | A61J 11/0085 |
| | | | 215/11.4 |
| 2011/0036801 A1* | 2/2011 | Krans | A61J 9/00 |
| | | | 215/11.1 |
| 2011/0087078 A1 | 4/2011 | Zemel | |
| 2012/0232801 A1 | 9/2012 | Kaplan | |
| 2014/0207024 A1 | 7/2014 | Aron | |
| 2015/0196247 A1* | 7/2015 | Lau | G01F 15/063 |
| | | | 600/301 |
| 2015/0224349 A1* | 8/2015 | Curtis | A41D 31/125 |
| | | | 2/455 |
| 2015/0335533 A1* | 11/2015 | Pineda | A61J 9/00 |
| | | | 215/11.1 |
| 2016/0137483 A1* | 5/2016 | Pfeiffer | G01F 17/00 |
| | | | 600/509 |
| 2018/0197629 A1* | 7/2018 | Zhou | A61J 9/00 |
| 2019/0096224 A1* | 3/2019 | Shoham | G08B 21/182 |

FOREIGN PATENT DOCUMENTS

| | | |
|---|---|---|
| JP | 2007526031 A | 9/2007 |
| WO | 2013187763 A1 | 12/2013 |
| WO | 2014015180 A1 | 1/2014 |

* cited by examiner

FEEDING SYSTEM FOR AN INFANT AND METHOD OF USING SUCH A SYSTEM

This application is the U.S. National Phase application under 35 U.S.C. § 371 of International Application No. PCT/EP2016/070298, filed on Aug. 29, 2016, which claims the benefit of International Application No. 15184981.7 filed on Sep. 14, 2015. These applications are hereby incorporated by reference herein.

FIELD OF THE INVENTION

The present invention relates to a feeding system for an infant and to a method of using such a feeding system.

BACKGROUND OF THE INVENTION

Feeding systems for infants typically include a bottle for milk, a liquid infant formula or other liquids, generally referred to as a fluid. During feeding, the fluid is dispensed to the mouth of the infant. To ensure secure feeding and well-being of the infant, a number of parameters regarding the bottle content should be monitored. Common feeding systems often provide only one parameter such as temperature of the bottle contents without giving further information. As a consequence, parents tend to feeling insecure and helpless.

WO 2013/187763 A1 discloses a method and system for monitoring a feeding pattern of an infant wherein the system is configured to measure one or more parameters including the amount of liquid the bottle contains and to send the measured data to an external device such as a computer, smartphone etc. A message such as an alert or a report based on the measured values is provided.

SUMMARY OF THE INVENTION

It is an object of the present invention to provide a system for feeding of an infant and a method of using such a system that improves the known feeding systems.

To this end, a first aspect of the present invention is directed to a feeding system for infants comprising a bottle for storing and releasing a fluid, at least one sensor arranged in or at the bottle for measuring one or more bottle parameters, a data processing unit for processing the measured bottle parameters to generate an advice related to at least one bottle parameter, and an indicator for issuing said advice to a user of the feeding system.

According to another aspect of the invention, a method of monitoring the feeding of an infant by use of a feeding system comprises the following steps: receiving one or more bottle parameters measured by at least one sensor during feeding an infant from the bottle, generating an advice related to one or more bottle parameters, and issuing the advice for adjustment of one or more of the bottle parameters.

Preferred embodiments of the invention are defined in the dependent claims. It shall be understood that the claimed methods, processor, computer program and medium have similar and/or identical preferred embodiments as the claimed system and as defined in the dependent claims.

A major drawback of known systems is the absence of directions what to do when the alert given out by the feeding system is a warning or a bad report. A bad report in this regard could for example be that during a measured time the content of the bottle has not been consumed, thus leading to underfeeding of the infant. In other words, parents may have information about a problem but they do not have any guidance how to solve the problem.

By surveying parameters regarding the bottle contents a multitude of information can be provided to a user. Based on this information it is possible to guide the user by generating advice or directions and displaying them to the user. The user not only gets information which might be confusing but a clear advice or directions what to do if one or more of the parameters measured is out of a predetermined range or deviates from a predetermined value. Those values and ranges can be for example derived from previous measurements, from recommendations given out by an expert like a doctor or a nurse, or from data collections determined from tests.

The terms "advice", "guidance" or "directions" in this context may all be understood as generally having the same meaning as any information displayed to the user stating what to do. The information thus goes beyond simple alerts/alarms or reports which only display values and possible problems due to values out of ranges. "Advice", "guidance" or "directions" may comprise actions to be taken by the user to attend to the respective problem. Further, "advice", "guidance" or "directions" may also be understood and include a defined guideline or instruction how to change the setup of the feeding system when a condition is met which might e.g. be dangerous for the infant.

Further, the term "liquid" as used herein shall generally be understood as "fluid".

There are various parameters which directly influence the health of the infant and which can easily be monitored by the proposed system. One of those is the temperature of the bottle contents. The temperature should not be too cold to avoid indigestion and on the other hand not too hot to avoid burns and injury in the mouth and gullet of the infant. Besides, it is desirable to establish a certain uniformity and rhythm regarding feeding times which can easily monitored by the inventive system. It will remind the care person to feed in time and the correct amount. During feeding, the infant has to be monitored closely to make sure that the amount of liquid delivered to the infant is suitable to the condition of the infant. The time needed to empty the bottle might differ from time to time depending on the health state of the infant, fatigue, agitation and other factors. It is important for feeding persons to get information and advice, for example to choose a suitable teat from a variety of accessories to meet the requirements of the infant.

The predetermined values can further be individualized for the specific infant to be fed from the feeding system to give additional security and potential for optimization.

Generally, the at least one sensor can be arranged anywhere and anyhow in or at the bottle. Hereby, the location and the way of arrangement will mainly depend on the kind of sensor and the kind of bottle parameter that shall be measured. It shall be noted that the expression "in or at the bottle" hereby includes locations inside the bottle, locations outside the bottle, locations in or at any surface of the bottle, integrations into the material of the bottle, locations at separate elements that are coupled to the bottle (such as a teat a screw ring at the opening of the bottle to hold the teat to the bottle, or a sleeve), etc.

In one embodiment, the at least one sensor, the data processing unit, and the indicator are mounted in or at the bottle. Thus, the system is compact and easy to handle without the drawback of cables, plugs or other data transfer means. The indicator arranged directly on the bottle gives the parents or the person caring for the infant a direct control about the drinking behavior and possible problems during feeding.

In another embodiment, the system further comprises a holder wherein the at least one sensor, the data processing unit, and the indicator are arranged in or at said support which is detachably or permanently connected to the bottle. Especially the detachable connection to the bottle is a positive aspect of this embodiment, since the bottle itself can easily be removed and cleaned for example in a dishwasher, or replaced by a new bottle if the old one is not suitable for safe use any more.

According to another embodiment of the invention, the feeding system further comprises a bottle communication unit in or at the bottle for wireless or wired communication with at least one user device. The at least one user device comprises a device communication unit for communication with the bottle communication unit. The user device is the main source of information for the parents or the person caring for the infant. Thus, by communication between the feeding system, especially the bottle and the user device, the information about the bottle contents and the drinking behavior of the infant as well as the advice about adjustment of parameters can easily be perceived and followed.

According to yet another embodiment, the at least one sensor and the data processing unit are arranged in or at the bottle and the indicator is arranged in or at the user device. In this embodiment, the user device can be a rather simple and cheap device which is mainly used for displaying the information or advice.

According to another advantageous embodiment of the feeding system, the sensor is arranged in or at the bottle and the rest of the components, especially the data processing unit and the indicator, are arranged in or at the user device. In this embodiment, the main task of the bottle is generation of data and the rest is obtained by the user device which might for example be a more sophisticated device like a smartphone or a tablet computer running a program or an application suitable for processing the measured data and generating the advice. The bottle is then relatively cheap and easy and can be designed to be dishwasher proof to be easy to clean.

According to advantageous embodiments of the invention, the at least one sensor can be a pressure sensor, a flow sensor, a mass sensor, a temperature sensor, a sensor for opening/closing of the bottle, a timer, a stop watch, or an arbitrary combination of two or more of said sensors. With said sensors, the feeding behavior of the infant can be closely monitored, especially with regard to the consumption of food and the time needed for consumption. Additionally, the temperature can be measured, thus making sure that the content of the bottle is not too hot or too cold for the infant. If the last opening or closing cycle or the bottle is monitored, the shelf life of the contents can be derived. This is especially important if the food has not been prepared by the person later feeding the infant.

In an embodiment a measurement of the flow from the bottle and the consumption of the infant related to time is performed. If this parameter is monitored it is on the one hand possible to control the individual suction behavior and to adjust it if necessary, on the other hand the consumption by session, day, week etc. can be monitored and used for statistical purposes. The advice related to this parameter will be helpful to choose the teat of the bottle according to the needs of the infant. Secure feeding without the risk of choking (flow too high) or high suction effort (flow too low) can thus be achieved.

According to yet another advantageous embodiment of the invention, the indicator can be one of an optical, acoustical, or tactile indicator or a combination thereof. Optical information can be displayed on a screen, for example on the screen of a smartphone; acoustical information can be given out by a speaker or tactile information can be generated in form of a vibrational signal. Common smartphones and tablet computers are apt to give out the respective signals without need for any special equipment.

In another embodiment the feeding system further comprises an environmental sensor, in particular one or more of a light sensor, a microphone, and an air flow measurement sensor, arranged in or at the bottle and/or a user device for measuring an environmental parameter, wherein said data processing unit is configured to use the measured environmental parameter to determine a preferred environmental condition (e.g. the lighting condition, noise condition, air flow condition). One or more of such sensors may already be available at such a user device, e.g. at a smartphone comprising a camera (as light sensor) and a microphone.

Advantageously, the user device can be one of a smartphone, a tablet computer, a laptop, a wrist-worn device (e.g. a watch, heart rate monitor, etc.) or a personal computer. At least one of those devices is generally available in nearly any household nowadays. In this regard, an improved feeding system giving a high degree of security and protection to the parents or person caring for the child is achieved.

According to another embodiment the system further comprises a combination of a mass sensor or a flow rate sensor with a timer, wherein said mass sensor is configured to measure a change in mass over time and the flow sensor is configured to measure a change in flow over time. This enables a rather accurate measurement of the flow rate of the fluid, which may then be used to give advice to the user, e.g. to take a certain measure to increase or decrease the flow rate, if considered necessary.

These and other features and advantages of the invention will be more fully understood from the following detailed description of certain embodiments of the invention, together with the accompanying drawings, which are meant to illustrate and not to limit the invention.

DETAILED DESCRIPTION OF THE EMBODIMENTS

Figure 1:
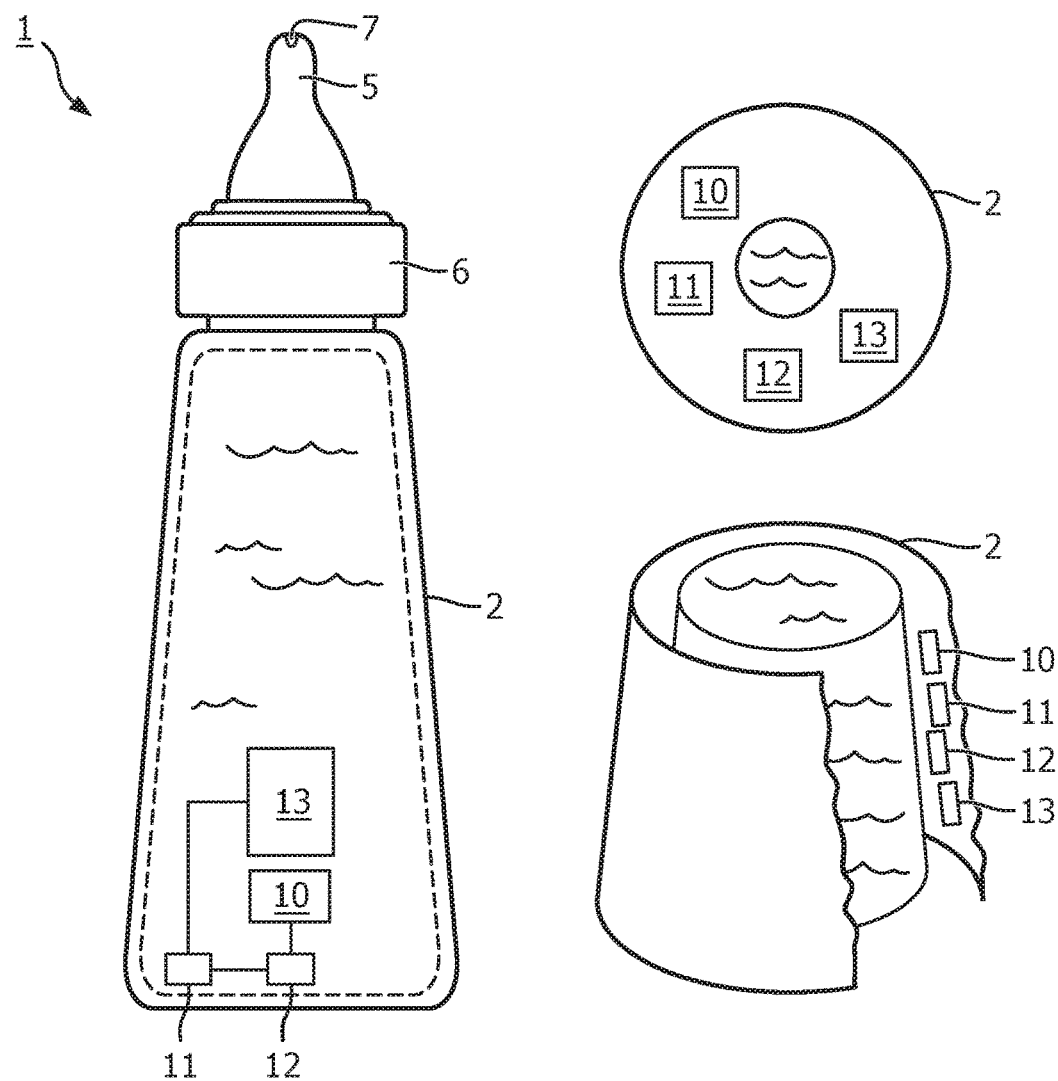
FIG. 1 shows a first embodiment of the feeding system according to the invention.

In FIG. 1 a first embodiment of a feeding system 1 for an infant according to the invention is shown. Generally, the feeding system 1 comprises a bottle 2 which may be designed and shaped like common feeding bottles known from the state of the art, which are designed to hold a liquid like milk or a feeding formula in a hollow body of the bottle. The bottle's material can be a glass or plastic or any material suitable for containers to store and heat food. The bottle 2 further comprises a teat 5 which is arranged on the open end of bottle 2 and which can be fixed to the bottle 2, for example by a teat ring 6. The teat ring 6 can be screwed on the open end of the bottle 2 on a thread (not shown) to hold the teat 5 in place. Any other suitable releasable mechanism is also possible. The teat 5 is formed from a soft deformable material like silicone or the like and comprises at least one opening 7 for dispensing the liquid to the infant's mouth.

According to a first embodiment of the invention, the bottle 2 comprises at least one sensor 10 which is arranged in or at the bottle 2. "Arranged in or at the bottle" in this regard should be understood as "in direct connection to the bottle 2" or "integrally with the bottle 2" or "inside the bottle 2" (e.g. on an inner surface). For example, the sensor 10 may be integrated in the bottle 2 between two layers of bottle 2. In this case, an inner body of the bottle 2 holds the liquid contents, whereas the outer layer serves as cover for the sensor 10 and other components described below. By this protection, the bottle 2 is easy to clean and even can be designed to be dishwasher proof. The sensor 10 may also be arranged at another element, such as the teat 5 or the teat ring 6, which is arranged at the bottle 2.

Alongside the at least one sensor 10, a data storage 11, a data processing unit 12 and an indicator 13 are similarly arranged in or at the bottle 2. The at least one sensor 10 can be one of or a combination of two or more selected from a pressure sensor, a flow sensor, a mass sensor, a temperature sensor, a sensor for opening/closing of the bottle, a timer, or a stop watch.

A pressure sensor can be used to measure the pressure inside the bottle. A temperature sensor can be used to measure the temperature, in particular indirectly from the outside, e.g. through the bottle by infrared radiation. Alternatively, a temperature sensor inside the bottle for direct measurement of temperature may be used.

Some sensors, in particular the pressure sensor and, optionally, the temperature sensor, measure from inside the bottle. The other sensors preferably measure from outside the bottle.

In case there is more than one sensor 10, these sensors 10 can all be arranged in a similar manner as described before. The aforementioned components are connected to each other to allow data to be transferred from one component to others. The at least one sensor 10 is at least connected to the data storage 11 and to the data processing unit 12. The data processing unit 12 gets data from the at least one sensor 10 and from the data storage 11 and thus is connected to them. The respective data, results, alerts, directions etc. are sent to the indicator 13 which therefore needs at least to be connected to the data processing unit 12.

The data storage 11 is designed to store data measured by the at least one sensor 10 as well as predetermined values for comparison. The data storage 11 can be any suitable storage device which can be connected to the bottle 2 either integrally or removably. In case the data storage 11 is removable, it can be a common storage device like an SD-card. Generally the data storage 11 is a commonly used electronic component.

The data processing unit 12, which can also be arranged in the bottle 2 as described above, is configured for carrying out comparisons between measured values and predetermined values stored in the data storage 11. Furthermore, the data processing unit 12 may generate an alert or a warning, if the measured values differ from the predetermined values and further generates a guidance, direction or suggestion for the user of the feeding device 1 how to attend to the problem, e.g. by adjusting the configuration of the bottle 2 or by modifying the contents of the bottle 2. Furthermore, the data processing unit 12 delivers the directions to the indicator 13. An example of this process will be discussed in more detail with reference to FIGS. 4A and 4B below.

The indicator 13 can be for example an optical display, a speaker or a vibrating unit. The indicator 13 can also be a combination of one or more of the aforementioned components. In an optical display, alerts and directions can be displayed, alongside with optical signals like flashing LEDs, colored elements or the like. When an optical alert is given out, also a vibrational and/or acoustical warning can be emitted. This is for example useful when the optical display is turned away from the user during feeding of the infant. The acoustical signal and/or the vibration of the bottle 2 can in any case be perceived by the user.

Figure 2:
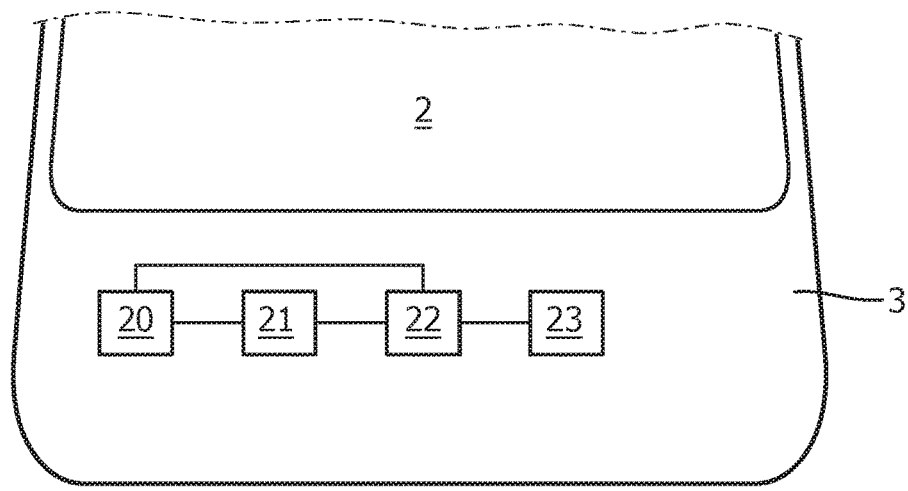
FIG. 2 shows a second embodiment of the feeding system according to the invention.

In FIG. 2 a second embodiment of the feeding system 1 of the invention is shown. In this embodiment, electronic components, including the at least one sensor 20, the data storage 21, the data processing unit 22 and the indicator 23, are arranged in a holder 3, which is removably connected to the bottle 2. The bottle 2 can simply be slid into holder 3 or alternatively screwed in, clipped in or fastened by a clamp. As a special advantage of this embodiment, the bottle 2 can have a very simple structure. If the holder 3 is designed accordingly, the bottle can be any commercially available bottle. It can be removed from the holder 3 and for example placed into a dishwasher for cleaning. The electronic components housed in the holder 3 thus do not need to be specially protected. The holder 3 can easily be cleaned by a moist cloth; it has not necessarily to be put into the dishwasher, since it does not come into contact with the liquids in the bottle 2.

The electronic components according to FIG. 2 can be similar or identical to the components explained with reference to FIG. 1, where they have already been described. Their function is also comparable to the feeding system according to FIG. 1.

Figure 3A:
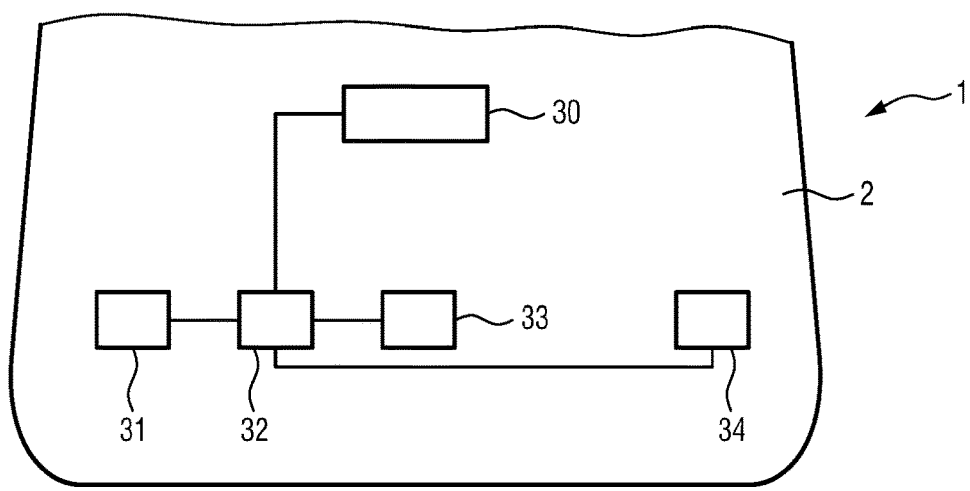
FIGS. 3A and 3B show further embodiments of the proposed feeding system comprising a user device.
Figure 3A:
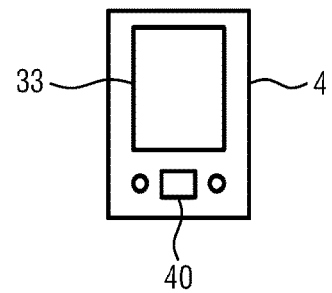
Figure 3B:
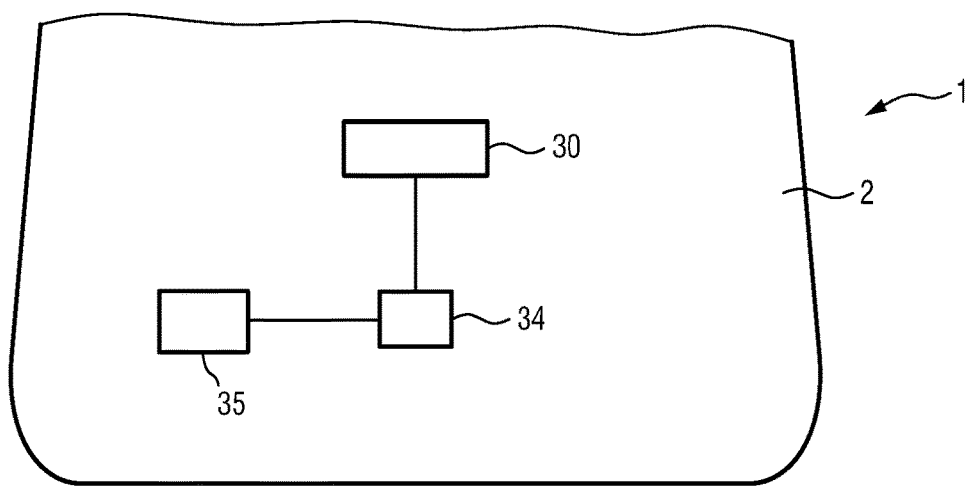
Figure 3B:
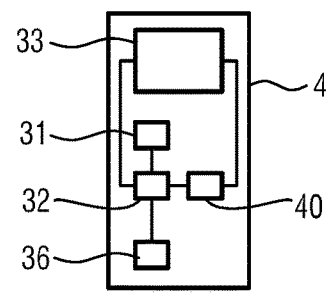

In FIGS. 3A and 3B, two further embodiments of feeding systems 1 according to the invention are shown. According to these embodiments the feeding system 1 further comprises a user device 4. The user device 4 can, for example, be a smartphone, a tablet computer, a laptop, a wrist-worn device (e.g. a watch or heart rate monitor) or notebook or a personal computer, but is not limited to any of these examples.

According to FIGS. 3A and 3B the electronic components are arranged in the bottle 2 similar to the arrangement in FIG. 1. It is easily understood that alternatively the embodiment of FIG. 2 can be combined accordingly with the user device 4 according to FIG. 3A and FIG. 3B.

In FIG. 3A, an embodiment of a "smart bottle" 2 as shown in FIG. 1 is described in combination with a simple user device 4, whereas in FIG. 3B a "simple bottle" 2 corresponding to a smart user device 4 is shown.

The bottle 2 according to FIG. 3A comprises again the electronic components of at least one sensor 30, data storage 31, data processing unit 32 and optionally at least one indicator 33. Furthermore, the bottle 2 comprises a bottle communication unit 34 which transmits information to the user device 4. This information can be the data measured by the at least one sensor 30, a calculated value from comparison to predetermined values, an alert, if values are out of predetermined ranges, and directions or guidance regarding necessary actions to be taken by the user of the feeding system 1.

The user device 4 accordingly comprises a device communication unit 40 which receives the information from the bottle 2 and displays said information to the user. The user device 4 according to this embodiment can be a rather simple device which is only designed to display the information provided by the bottle 2. It can hold a speaker and/or a vibrational unit to give out not only optical alerts. The information given on the indicator 33 can be the alert or warning and after alerting the user, precise directions how to attend to the problem.

The embodiment shown in FIG. 3B comprises, in contrast to FIG. 3A, a rather simple bottle 2, which only holds at least one sensor 30 and the bottle communication unit 34. Again, the sensor 30 measures the bottle values and transmits the bottle values via the bottle communication unit 34 to the user device 4. In the user device 4, all other electronic components—data storage 3, the data processing unit 32 and the indicator 33—are present. These components are e.g. part of a commonly used smartphone or the like. In this regard, the comparison and calculation of the values and the generation of the directions for the user are carried out by an application installed on the user device 4 and which can for example also run on a tablet computer or on a laptop. The bottle 2 with only a few electronic components is cheap and easy to produce and also easy to clean.

The embodiments according to FIGS. 3A and 3B have different advantages as is apparent from the different bottles 2 and the different user devices 4. In the embodiment according to FIG. 3A, the bottle 2 is quite "smart", whereas the user device 4 is very simple. This embodiment can be seen in line with the embodiment according to FIG. 1 with the additional user device 4. The external user device 4 is advantageous as it enables the user of the feeding system 1 to have the display in clear view even when the indicator 33 on the bottle 2 is not visible (bottle 2 turned, display covered by hand of user etc.). The indicator 33 on the bottle 2 could also be omitted due to the displaying function of the user device 4.

In contrast to this, the feeding system 1 according to FIG. 3B comprises a very simple "stupid" bottle 2 and a smart user device 4. In this regard, "smart" is to be seen in relation to common mobile phones which nowadays perform a lot of functions which go far beyond the relatively easy comparison of values and generation of information on a display. A user device 4 like a smartphone, a tablet computer or a notebook is present in nearly any household nowadays, making it very easy to run the application and use the feeding device 1 according to the invention.

Optionally, as shown in FIG. 3B, one or more environmental sensors 35, 36 may also be provided in or at the bottle 2 and/or in or at the user device 4 for measuring an environmental parameter, such as lighting condition, noise condition, air flow condition. In particular, one or more of a light sensor, a microphone, and an air flow measurement sensor may be provided for performing a measurement of an environmental parameter, which may then be used to determine a preferred environmental condition of the infant for getting fed. One or more of such environmental sensors 35, 36 may also be provided in other embodiments of the feeding system.

A light sensor may be used to check in which conditions the infant is fed. If the infant prefers being fed in a darker/lighter room, a corresponding advice can be given to the user. A microphone can be used to measure the environmental noise to check in which environmental noise condition the infant prefers being fed (e.g. in silence, with music, with talking, etc.). Further, a microphone may be used to measure the breathing rhythm of the infant. Together with the pressure measurement in the bottle this makes it possible to record the breathing and sucking rhythm of the infant which can be used to give more in depth advice. If it is not possible to measure it with a microphone an air flow measurement may be used for this purpose.

Figure 4A:
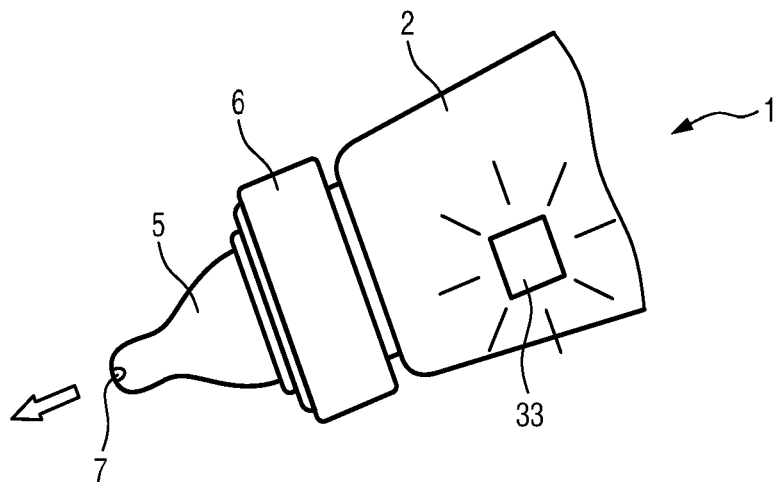
FIGS. 4A and 4B show another embodiment of the feeding system with an exemplary suggestion of changing the teat.
Figure 4B:
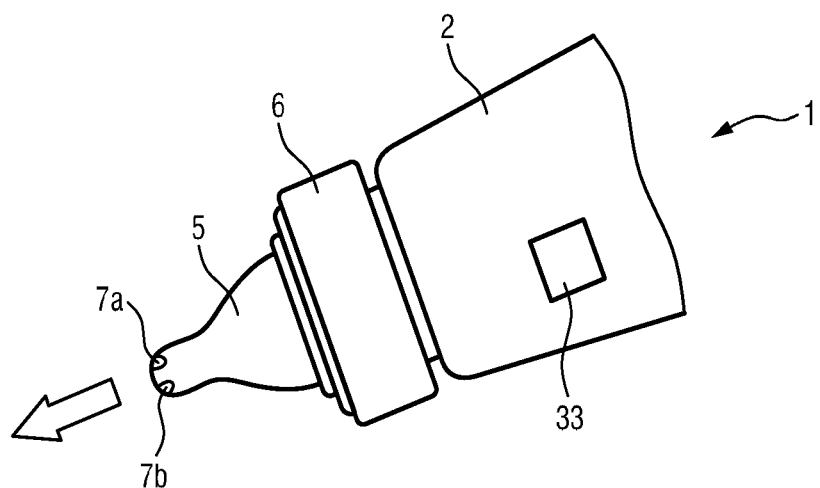

With reference to FIGS. 4A and 4B, another embodiment of the invention is shown, displaying an exemplary problem regarding the flow from bottle 2 and suggestions for the solution of the problem.

In FIG. 4A, a bottle 2 according to the present invention with an indicator 43 is shown. As can be seen in FIG. 4A, the indicator 43 is flashing a warning light to alert the user of the feeding system 1 that there is be a problem. On the user device 4 (not shown in FIGS. 4A and 4B), a message is displayed giving more details, for example by the phrase "flow from the bottle is not sufficient". Alongside with the information that the flow is not sufficient, the user device 4 then provides the user with advice or directions how to attend to the problem. This advice could for example be the recommendation to change to a teat 5 which allows an increased flow. Alternatively, the user could be invited to check the contents of the bottle 2 for texture or check whether the teat 5 is blocked.

As can be seen in FIG. 4A, the teat 5 has only one opening 7 which allows only a small quantity of liquid to be dispensed. The amount of liquid is shown by the arrow in FIG. 4A. Accordingly, in FIG. 4B the flashlight in the indicator 43 has stopped since the teat 5 has been replaced by a different one having two openings 7a and 7b, which allow a much higher flow from the bottle 2. The higher flow from the bottle 2 is marked by a thicker arrow compared to the arrow in FIG. 4A.

It can be understood that the indicator 33 not necessarily has to be present on the bottle 2 but can also be part of the user device 4 only. The warning would then be displayed on the user device 4. Likewise, any alert, message, advice, guidance or directions of use can be displayed.

The flow rate may generally be measured by a dedicated flow rate sensor, in particular by a combination of a mass sensor or a flow rate sensor with a timer. Said sensors are configured to measure a change in mass or flow over time. Alternatively, from the pressure, mass or flow sensor and the acoustical sounds it is generally possible to determine the drinking rhythm of the infant, which information can be used to give advice how to improve the drinking behavior of the infant.

Figure 5:
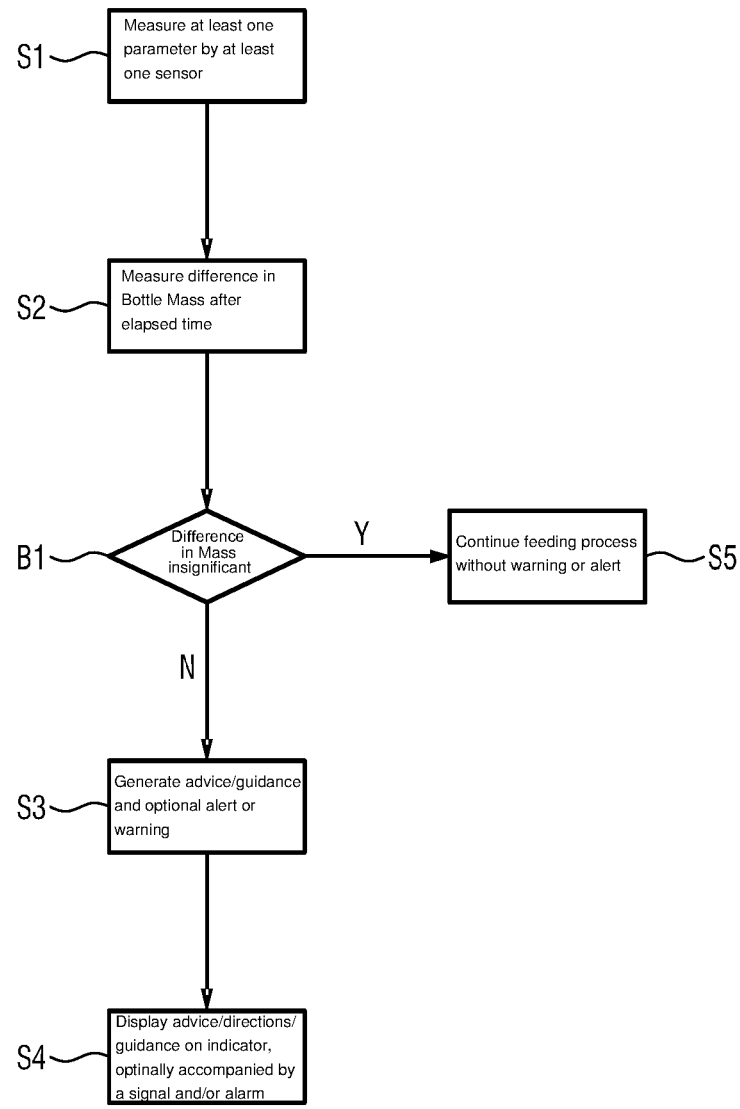
FIG. 5 shows a flowchart of an embodiment of the method according to the invention.

The process for evaluation of the values which lead to display of the directions for the user are shown in the flowchart according to FIG. 5.

A first step S1 is the measurement of at least one parameter associated to the contents of the bottle 2 by at least one sensor 10, 20, 30. With regard to the example of FIGS. 4A and 4B, this can be a mass $M_1$ of the bottle 2 at a time $T_1$ when feeding starts. After a time interval $\Delta T$ has lapsed, the mass of the bottle 2 is checked again ($M_2$) and the difference $\Delta M$ is compared in step S2 to a predetermined value stored in the data storage 11, 21, 31. The comparison is carried out by the data processing unit 12, 22, 32. Depending on the result the flow chart splits into two branches at the branching point B1. When the comparison does not result in significant differences from the predetermined value, the feeding process will continue without warning or alert (step S5).

If the result of the comparison differs from the predetermined value, optionally an alert or a warning and in any case an advice, directions or guidance is generated in step S3. In case the infant has not been drinking enough (in other words: the mass difference $\Delta M$ during the time interval $\Delta T$ is too small), the data processing unit 12, 22, 32 will optionally generate a warning and in any case give an advice, a direction or guidance regarding the size of the teat 5, for example: "Please change to teat with higher flow rate" or "Please use teat no. X", wherein X refers to a teat model to be selected from a range of accessories which are part of the scope of delivery of the feeding system 1. Said advice, guidance or directions are then displayed on the indicator 13, 23, 33, optionally accompanied by an acoustic signal, a flashlight, a vibrational alarm or the like, in step S4.

The predetermined values used for comparison to the measured bottle parameters can be results of measurements or comparisons derived from earlier collection of data, for example from the last feeding cycle, or from cumulated or averaged values of the last day, the last week, month etc. Furthermore, values from databases can be used, for example related to known drinking behavior of a control group of infants of same age, same weight or same family. Medical staff like the pediatrician consulted by the parents can also recommend how to set the feeding parameters.

In analogy to the flow from the bottle 2, any other parameter of the bottle 2 can be handled similarly. Further examples can include directions regarding preparation of the food:

recording of the last opening/closing of the bottle 2 can result in a direction to discard the contents due to exceedance of shelf life;

measurement of temperature and corresponding directions to warm or cool the bottle 2;

directions for shaking the bottle 2 when mixing of food from various ingredients is performed (to make sure that the ingredients mix well, but to avoid shaking to much to keep the amount of bubbles low).

Other examples can attend to the process of feeding itself:

measurement of the flow from the bottle 2 (change of mass over time) as described above, but also observing different aspects like check of texture of bottle contents, blocking of teat 5 etc.;

measurement of pressure in bottle 2 and/or of suction pressure to make sure that the infant can drink easily but not excessive;

measurement of feeding time and duration to avoid disturbance of the child due to irregular feeding intervals.

Other types of sensors to cover yet other bottle parameters can be present to widen the range of possibilities to control the feeding of the infant.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A feeding system for infants, comprising:
   a bottle for storing and releasing a fluid,
   a set of two or more teats having different flow rates, each of the teats being configured to be arranged on an open end of the bottle,
   at least one sensor integrated in the bottle between two layers of the bottle, the sensor configured to measure one or more bottle parameters associated with contents of the bottle,
   a data processing unit integrated in the bottle between the two layers of the bottle, configured to process the measured bottle parameters to generate an advice to a user regarding the teat, and
   an indicator integrated in the bottle between the two layers of the bottle, configured to issue said advice to said user of the feeding system, and
   wherein an inner body of the bottle is arranged to hold the fluid and an outer layer is arranged to cover the at least one sensor, the data processing unit and the indicator, and
   wherein the at least one sensor is selected from the group consisting of a pressure sensor, a flow sensor, a mass sensor, a temperature sensor, a sensor for opening/closing of the bottle, and a stopwatch.

2. The feeding system according to claim 1,
   further comprising a data storage for storing the measured bottle parameters, predetermined data, resulting data and algorithms.

3. The feeding system according to claim 1,
   wherein the at least one sensor, the data processing unit and the indicator are arranged in or at the bottle.

4. The feeding system according to claim 1,
   further comprising a holder wherein the at least one sensor, the data processing unit and the indicator are arranged in or at the holder which is detachably or permanently connected to the bottle, wherein the bottle is arranged to slide into the holder.

5. The feeding system according to claim 1,
   further comprising a bottle communication unit in or at the bottle for wireless or wired communication with at least one user device comprising a device communication unit.

6. The feeding system according to claim 5,
   wherein the at least one sensor and the data processing unit are arranged in or at the bottle and the indicator is arranged in or at the user device.

7. The feeding system according to claim 5,
   wherein the at least one sensor is arranged in or at the bottle and the data processing unit and the indicator are arranged in or at the user device.

8. The feeding system according to claim 1,
   wherein the indicator is one of an optical, acoustical or tactile indicator or a combination thereof.

9. The feeding system according to claim 1,
   further comprising at least two environmental sensors including a microphone and at least one of a light sensor and an air flow measurement sensor, arranged in or at the bottle and/or a user device for measuring an environmental parameter, wherein said data processing unit is configured to use the measured environmental parameter to determine a preferred environmental condition.

10. The feeding system according to claim 1,
further comprising a combination of a mass sensor or a flow rate sensor with a timer, wherein said mass sensor is configured to measure a change in mass over time and the flow sensor is configured to measure a change in flow over time.

11. The feeding system according to claim 5,
wherein the user device is a smartphone, a tablet computer, a laptop, a wrist-worn device, or a personal computer.

12. A method of monitoring the feeding of an infant by use of a feeding system comprising a bottle for storing and releasing a fluid, a set of two or more teats having different flow rates, each of the teats being configured to be arranged on the open end of the bottle, and at least one sensor arranged in the bottle for measuring one or more bottle parameters associated with contents of the bottle, the method comprising:
receiving the one or more bottle parameters measured by the at least one sensor integrated in the bottle between two layers of the bottle, during feeding of an infant from the bottle,
generating an advice derived by a data processing unit integrated in the bottle between the two layers of the bottle regarding the teat based on the measured bottle parameters, and
issuing the advice to a user of the feeding system via an indicator integrated in the bottle between the two layers of the bottle.

13. The method according to claim 12 wherein the method is performed by one of an application or program present on at least one user device which is configured to carry out the method steps.

14. A non-transitory computer storage medium on which is stored computer program code instructions for execution of a method when when executed by a processor for providing control signals for carrying out the steps of the method as claimed in claim 12 when said computer program code instructions are carried out on said computer storage medium.

15. The method according to claim 13,
wherein the user device is a smartphone, a tablet computer, a laptop, a wrist-worn device, or a personal computer.

16. The feeding system according to claim 1,
further comprising a holder wherein the at least one sensor, the data processing unit and the indicator are arranged in or at the holder which is detachably or permanently connected to the bottle, wherein the bottle is arranged to screw into the holder.

17. The feeding system according to claim 1,
further comprising a holder wherein the at least one sensor, the data processing unit and the indicator are arranged in or at the holder which is detachably or permanently connected to the bottle, wherein the bottle is arranged to clip into the holder.

18. A feeding system for infants, comprising:
a bottle for storing and releasing a fluid,
a set of two or more teats having different flow rates, each of the teats being configured to be arranged on an open end of the bottle,
at least one sensor arranged in the bottle, configured to measure one or more bottle parameters associated with contents of the bottle,
a data processing unit arranged in the bottle, configured to process the measured bottle parameters to generate an advice to a user regarding the teat, and
an indicator arranged in the bottle, configured to issue said advice to said user of the feeding system, and
a holder, wherein the at least one sensor, the data processing unit and the indicator are arranged in or at the holder which, and wherein the bottle is arranged to slide into the holder.

19. The feeding system according to claim 18, wherein the holder is removably connected from the bottle.

20. The feeding system according to claim 18, wherein the holder is permanently connected to the bottle.

* * * * *